United States Patent
Rzesnitzek et al.

(10) Patent No.: US 7,494,464 B2
(45) Date of Patent: Feb. 24, 2009

(54) MONITORING SYSTEM FOR MONITORING THE PROGRESS OF NEUROLOGICAL DISEASES

(76) Inventors: Alexander Rzesnitzek, Im Kleestück 16, D-56070 Koblenz (DE); Eberhard Schmitt, Burqweq 44, D-56068 Koblenz (DE); Christian Reuter, Hauptstrasse 43, D-56412 Holler (DE)

( * ) Notice: Subject to any disclaimer, the term of this patent is extended or adjusted under 35 U.S.C. 154(b) by 0 days.

(21) Appl. No.: 10/815,455

(22) Filed: Mar. 31, 2004
(Under 37 CFR 1.47)

(65) Prior Publication Data

US 2004/0263617 A1     Dec. 30, 2004

(30) Foreign Application Priority Data

Sep. 21, 2001 (DE) .............................. 101 46 680.3
Sep. 17, 2002 (EP) .............................. 02 020 788.2

(51) Int. Cl.
*A61B 5/00* (2006.01)

(52) U.S. Cl. ........................................ 600/300; 128/920

(58) Field of Classification Search ......... 600/300–301; 128/903–905, 920; 348/14.01; 379/106.1–106.2
See application file for complete search history.

(56) References Cited

U.S. PATENT DOCUMENTS 5,801,755 A * 9/1998 Echerer .................... 348/14.01
5,950,632 A * 9/1999 Reber et al. .................. 128/898

* cited by examiner

*Primary Examiner*—Michael C Astorino
(74) *Attorney, Agent, or Firm*—Friedrich Kueffner

(57) ABSTRACT

The invention concerns a monitoring system for monitoring patients with disturbed motor function. The monitoring system is characterized by at least one observation station (3) with an electronic camera for recording video motion pictures and devices (10) for marking an object field to be covered by the camera (9), a storage device for the digital storage of video pictures of a patient, which are to be recorded at preselected intervals by the camera in the movement station, an image processing system for processing the video pictures recorded in time intervals to obtain a shortened video picture sequence, and a video display device for displaying the video picture sequence.

12 Claims, 2 Drawing Sheets

MONITORING SYSTEM FOR MONITORING THE PROGRESS OF NEUROLOGICAL DISEASES

BACKGROUND OF THE INVENTION

1. Field of the Invention

The invention concerns a monitoring system for monitoring the progress of neurological diseases, especially for monitoring patients with disturbed motor function.

2. Description of the Related Art

The tasks involved in monitoring the progress of neurological diseases include that of observing the effect of drug administration. For example, in some patients with Parkinson's disease, a reduction of the duration of action is observed after about four years, which initially can still be compensated by reducing the time intervals between drug doses. In the further course of the disease, the duration of action changes irregularly and hyperkinesia may even appear after the drug has been taken, which can be so violent in individual cases that it constitutes an indication for epileptic surgical intervention.

Fluctuations of drug effects are thus a frequent reason for hospitalization of patients with disturbed motor function to allow observation following drug intake. Observation periods spread over days in time intervals of, say, hours, are desirable. However, in everyday practice, this can scarcely be organized to a sufficient extent, even in the case of hospital treatment. Assessments are based on few samples, which, to make matters worse, are made by different persons on the basis of insufficiently standardized criteria.

SUMMARY OF THE INVENTION

The objective of the present invention is to improve the treatment options of neurological diseases, especially of patients with disturbed motor function.

This objective is achieved by a monitoring system, which is characterized by
- at least one observation station with an electronic camera for recording video motion pictures and devices for marking an object field to be covered by the camera,
- a storage device for the digital storage of video pictures of a patient, which are to be recorded at preselected intervals by the camera in the movement station,
- an image processing system for processing the video pictures recorded in time intervals to obtain a shortened video picture sequence, and
- a video display device for displaying the video picture sequence.

In this monitoring system, the patient goes at predetermined times after taking his medication, e.g., at intervals of about 1 hour, to the observation station, where he performs a specific type of movement he has previously agreed to perform in the object field covered by the camera, e.g., he walks along a path marked on the floor. The video information, which is possibly stored over a period of one day, is compressed by the image processing system. The attending physician can view the video motion pictures recorded at intervals in the observation station in immediate succession in the compressed video. There is no need for the physician himself to follow any observation schedule. The viewing of the compressed video picture sequence makes it possible to detect any changes in the movement of the patient more precisely than would be possible by direct observation of the patient at intervals of time. The system ultimately allows exact quantification and objectification of the fluctuation in effect. The quality of the monitoring of the progress of neurological diseases can be significantly increased with less input of personnel.

In a preferred embodiment of the invention, several observation stations and a central evaluation station that comprises the video display device are provided, wherein the central evaluation station contains the video display device and preferably consists of a computer networked with the observation stations. In turn, the individual observation stations can be equipped with a computer unit, which is connected to the electronic camera, whose video data it receives and preprocesses. Accordingly, this computer unit can constitute the storage device and the processing system and can be used for data communication with the central evaluation station.

In the preferred embodiment of the invention, the system is intended for the monitoring of a large number of patients, who visit at least one observation station at different times. In this case, the observation station has devices for automatic patient identification, and the storage device and image processing system are designed for patient-specific image storage and processing, i.e., they carry out the storage and processing in coordination with identification data and ultimately the patient data files.

In a further refinement of the invention, the video recording can be controlled by the electronic camera via the patient identification device. For example, the patient identification device can be equipped with a reading device for a transponder worn by the patient. After the transponder has been read and a certain waiting time has passed, during which the patient can move to the object field, the camera is activated, which can be indicated to the patient, e.g., by a light signal, whereupon the patient then carries out the stipulated movements.

In addition, it is advantageous to provide a programmable signaling device, which is carried by the patient and reminds him at preselected times to take his medication and to go to the observation station. In particular, this signaling device can be automatically programmed through suitable accessory devices on the basis of data input into the computer unit or the personal computer.

In other advantageous refinements of the invention, devices for the automatic coordination of observation times can be provided, which prevent double occupation of the observation stations and search for the alternative time for a patient that is optimum with respect to the administration of a drug.

It is advantageous to provide a device at the observation station for the output of information for the patient, e.g., a printer, which prints out a change in medication made as a result of the evaluation.

In a further refinement of the invention, the image processing system can be designed to go beyond sequencing to process the recorded images themselves. For example, the individual video motion pictures recorded at different times can be converted to time-lapse recordings that further shorten the sequence, or automatic comparisons can be made between the individual images, and, e.g., superimposed images can be displayed, which clearly bring out changes in the recorded movements.

BRIEF DESCRIPTION OF THE DRAWING

The invention will now be explained in greater detail with reference to a specific embodiment and to the accompanying drawings that illustrate this embodiment.

DETAILED DESCRIPTION OF THE INVENTION

Figure 1:
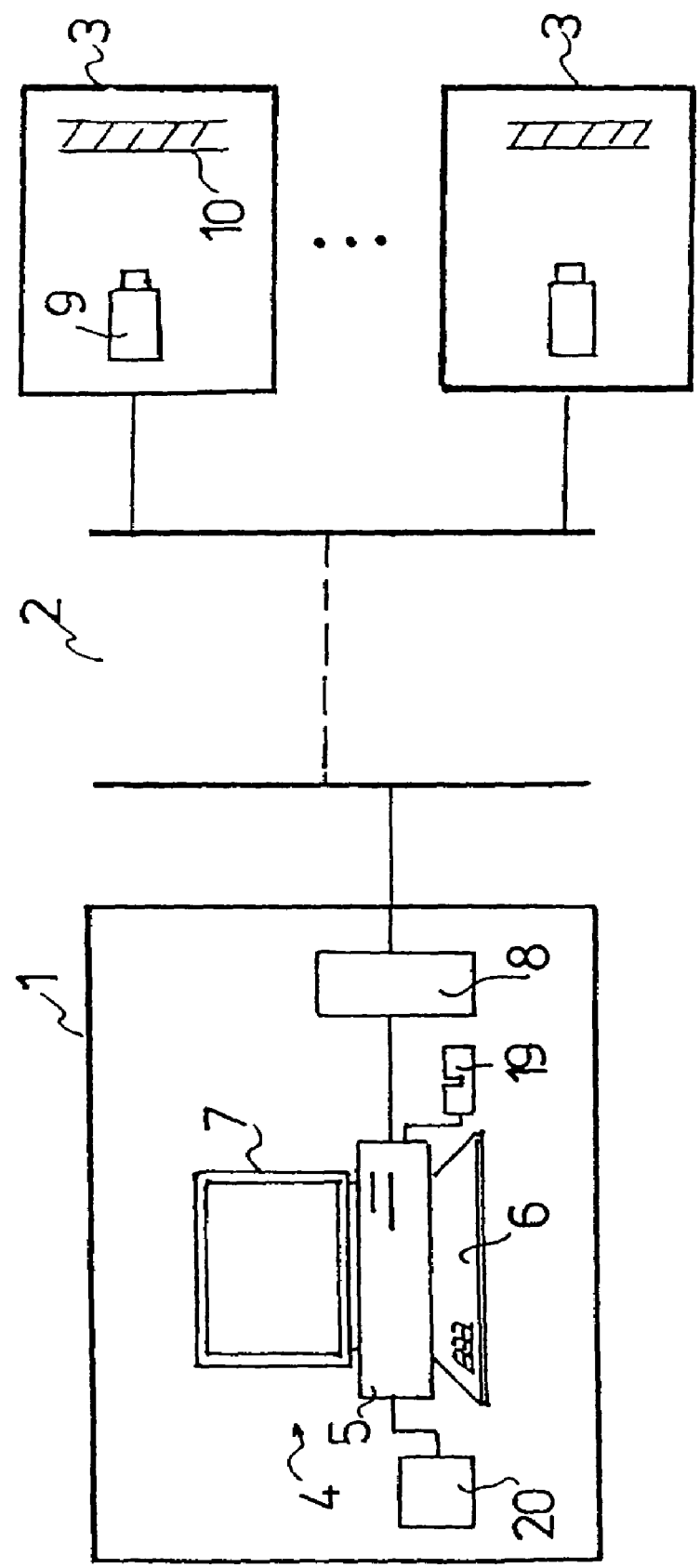
FIG. 1 shows a schematic representation of a monitoring system in accordance with the invention.

A central evaluation station 1 is connected with several observation stations, either directly or by a network 2, e.g., a network that includes the telephone network.

The central evaluation station 1 comprises a personal computer 4, which has the usual central computer unit 5, a monitor 6, and an input keyboard 7.

A modem 8 allows the personal computer 4 to establish data communication with the observation stations 3 via the network 2.

Each of the observation stations 3 is equipped with an electronic camera 9. An object field, at which the camera 9 is aimed, is marked by strip-shaped marking on the floor. The camera 9 is equipped with a wide-angle lens.

In addition, a card reader 19 and a programming unit 20 are connected to the personal computer.

The central evaluation station 1 may be located, e.g., in a hospital neurology unit. The observation stations 3 are located in different locations, e.g., in nursing homes or other facilities close to the patient.

Figure 2:
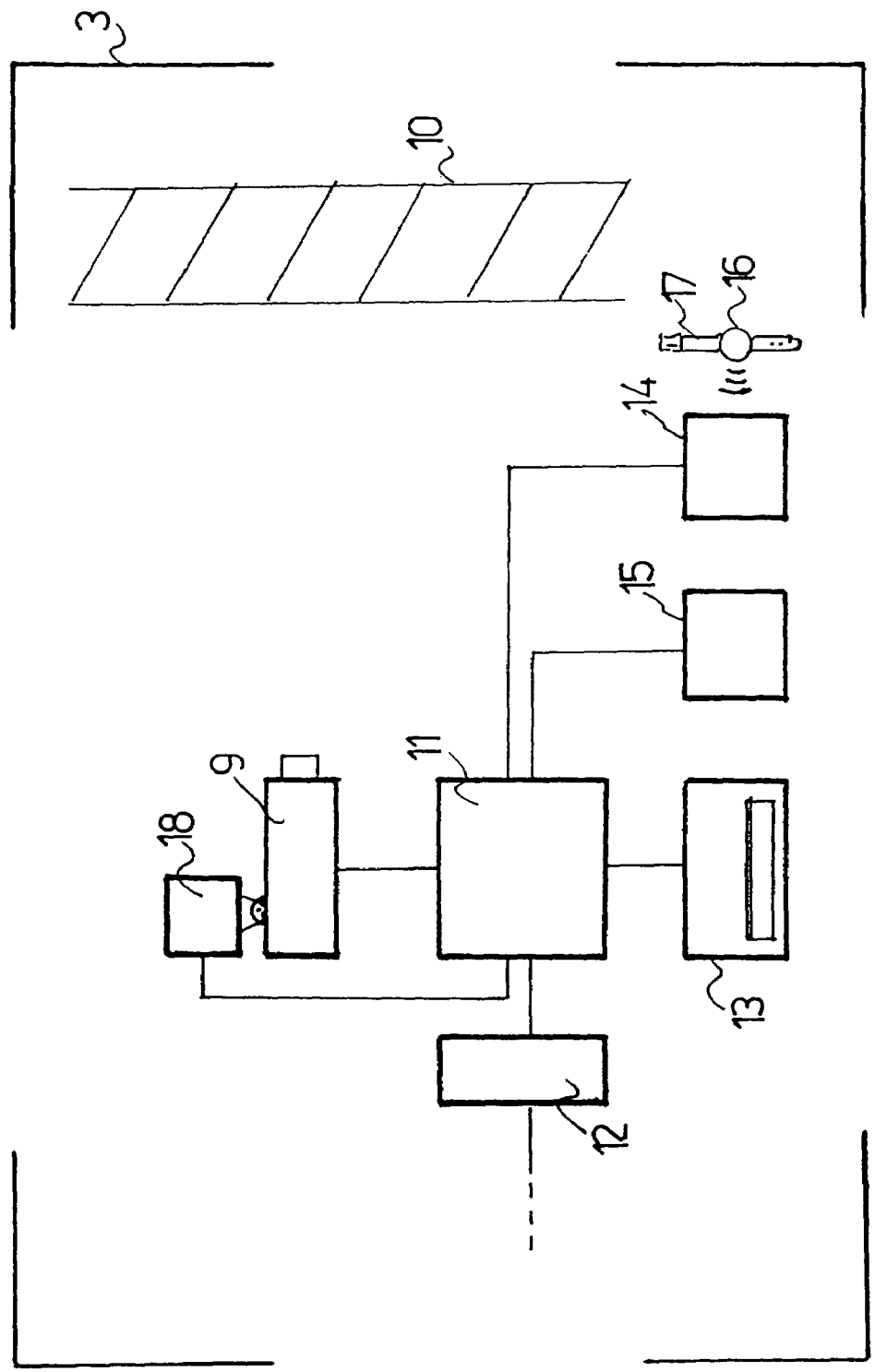
FIG. 2 shows an observation station used in the monitoring system of FIG. 1.

We now turn our attention to FIG. 2, which shows details of an observation station 3.

The electronic camera 9, which is equipped with a wide-angle lens and is suitable for recording motion pictures, is connected to a central computer unit 11, which, like the computer 4 in the central evaluation station 1, may consist of a personal computer.

The computer unit 11 constitutes a central control unit for the observation station 3. It is able to establish data communication with the personal computer 4 in the central evaluation station 1 via a modem 12.

In addition, a printer 13 is connected to the computer unit 11.

A transponder reader 14 and a programming unit 15 are also connected to the computer unit 11. The transponder reader 14 is used to read a transponder, which is contained in a unit 16 worn on a patient's arm. The unit 16, which is attached to an armband 17, also contains a signaling device, whose signals remind the patient to take medications and to go to the observation station 3 at predetermined times.

This signaling device can be automatically programmed via the programming unit 15 connected to the computer unit 11.

Finally, the camera 9 is equipped with a mechanical moving device 18, which can be controlled via the computer unit 11.

A patient to be treated reports for treatment to the central evaluation station 1 in a hospital, and, e.g., his insurance card is read in by the card reader 19, and a patient data file is established or opened. The patient is given an armband 17 with the unit that contains the transponder and the signaling device. The transponder supplies an identification code. Means are provided to prevent double assignment of this code. The code is assigned to the patient data file.

The attending physician uses the keyboard 6 to enter drug administration times and times at which the patient is to report to an appropriate treatment station 3. The signaling device in the unit 16 is automatically programmed via the programming unit 20 on the basis of this data. In the present embodiment, a plug connection is established between the programming unit 20 and the unit 16 to accomplish this programming. However, this type of programming could also be accomplished by wireless data exchange.

The signaling device furnishes signals to the patient to remind him to take his medication and later furnishes additional signals at predetermined time intervals to remind him to go to one of the treatment stations 3.

When he arrives at the treatment station 3, the patient reports by allowing his transponder to be read by the transponder reader 14. When the patient has been identified in this way, his patient data file is opened in the computer unit 11. In the present embodiment, this data file was previously transmitted by the central evaluation station 1 to the given computer unit 6 over the network 2.

At the same time, the camera 9 is activated by the identification, and after a delay, the operation of the camera is indicated by a signal light on the camera. It is advantageous to arrange the transponder reader 14 near the floor marking 10, so that the patient is already in the starting position for a previously stipulated movement to be performed in each observation cycle and can immediately begin this movement when the signal light on the camera goes on. In the present embodiment, the Parkinson's patient walks along the floor marking 10 in each observation cycle. Naturally, any other types of movements to be recorded by the camera 9 are also possible. If necessary, the camera can be designed to follow the subject by means of a mechanical moving device 18, and it is conceivable that this following motion could be controlled by motion detection or by the transponder signal, e.g., by installing transmitter-receivers that respond to the transponder along the floor marking 10.

The computer unit 11 digitally stores the patient-specific video signals it receives from the camera 9 in coordination with the clock time and stores the signals from observation to observation in the memory in such a way that, in a subsequent readout by the central evaluation station 1 on the monitor 7, a sequence of the video motion pictures that were recorded over periods of, e.g., 5 seconds, at intervals of, e.g., 1 hour, can be displayed in continuous form.

The attending physician evaluates these video pictures in the central evaluation station 1, e.g., on certain days, and as a result of the compression of the pictures collected at intervals over a period of days into picture sequences of short duration, he is able to care for a large number of patients at the same time.

The personal computer 4 of the central evaluation station 1 can be programmed for more extensive image processing for displaying the individual images of a sequence, e.g., by a time-lapse technique, for changing the order of images of the sequence, or for displaying several images of the sequence superimposed on one another.

After a certain treatment time, new medications, including the times of administration and observation times, can be established, which the attending physician enters by the keyboard 6. Information transmitted to the computer unit 11 over the network 2 can be printed out for the patient by the printer 13. In addition, the patient has the opportunity to automatically reprogram his signaling device at the observation station by means of the programming unit 15.

It goes without saying that the device functions that have been described are extensively supported by the programming of the personal computer 4 and the computer unit 11, and the software can be distributed between the two intercommunicating computers in different ways for the same function. For example, the image storage and processing could conceivably be carried out only in the central evaluation station 1. However, to limit the accumulation of data there, it is more convenient to do as much data preprocessing as possible in the observation stations 3.

The invention claimed is:

1. Monitoring system for monitoring the progress of neurological diseases, comprising
   at least one observation station (3) for a plurality of individually selectable patients, the observation station having an electronic camera (9) automatically controlled for recording video motion pictures, devices (10) for marking an object field to be covered by the camera (9), and devices for automatically identifying the patients, whereby the identifying devices are operative to automatically activate the camera to record the patient concerned, after identification, while the patient carries out predefined movements in the object field,
   an automatic storage device for the digital storage of video motion pictures of the patient selected pursuant to identification data, which are to be recorded at preselected time intervals by the camera (9) in the observation station (3),
   a video display device (7),
   an image processing system automatically processing the video motion pictures of each individual patient, upon request by an attending physician, recorded at the time intervals to be in uninterrupted sequence and displayed on the video display device, wherein the uninterrupted sequence of video motion pictures of the patient is of shorter duration than the time intervals,
   a mechanical moving device operative to move the camera to follow the patient in response to patient motion.

2. System in accordance with claim 1, comprising a plurality of observation stations (3) and a central evaluation center spatially separated from the observation stations, wherein the central evaluation center contains the video display device (7) and is configured to be connected with the observation stations for the purpose of data transmission.

3. System in accordance with claim 2, wherein the central evaluation center consists of a computer.

4. System in accordance with claim 3, wherein the computer is a personal computer (4).

5. System in accordance with claim 2, wherein the observation station contains a computer unit (11) connected to the electronic camera.

6. System in accordance with claim 5, wherein the computer unit (11) is provided for data communication with the central evaluation center (1) and contains the storage device and the processing system.

7. System in accordance with claim 1, comprising a programmable signaling device which is carried by the patient and produces signals that remind the patient to take his medication and/or to go to the observation station.

8. System in accordance with claim 7, further comprising devices (15, 20) for automatic programming of the signaling device on the basis of input data.

9. System in accordance with claim 1, further comprising devices for automatic coordination of observation times.

10. System in accordance with claim 1, wherein the image processing system is configured to go beyond sequencing to process the recorded images themselves.

11. System in accordance with claim 1, wherein the camera is moved by the mechanical moving device in response to motion detection.

12. System in accordance with claim 1, wherein the camera is moved by the mechanical moving device in response to transponder signals from a transponder worn on the patient.

* * * * *